(12) United States Patent
Jamison et al.

(10) Patent No.: US 11,739,636 B2
(45) Date of Patent: *Aug. 29, 2023

(54) METHOD AND APPARATUS FOR MEASURING CHARACTERISTICS OF FLUID IN A RESERVOIR

(71) Applicant: Halliburton Energy Services, Inc., Houston, TX (US)

(72) Inventors: Dale E. Jamison, Humble, TX (US); Kenneth Heidt Matthews, Kingwood, TX (US); Andrew D. Vos, Spring, TX (US); Sandeep D. Kulkarni, Kingwood, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 394 days.

This patent is subject to a terminal disclaimer.

(21) Appl. No.: 17/182,978

(22) Filed: Feb. 23, 2021

(65) Prior Publication Data

US 2021/0180449 A1 Jun. 17, 2021

Related U.S. Application Data

(63) Continuation of application No. 15/748,148, filed as application No. PCT/US2015/050450 on Sep. 16, 2015, now Pat. No. 10,947,843.

(51) Int. Cl.
*E21B 49/08* (2006.01)
*G01N 9/26* (2006.01)
(Continued)

(52) U.S. Cl.
CPC .......... *E21B 49/0875* (2020.05); *E21B 49/08* (2013.01); *G01N 9/26* (2013.01); *G01N 9/36* (2013.01); *G01N 33/28* (2013.01)

(58) Field of Classification Search
CPC . G01N 9/26; G01N 9/36; G01N 33/28; G01F 23/0007; G01F 23/14; G01F 23/161; E21B 49/0875
See application file for complete search history.

(56) References Cited

U.S. PATENT DOCUMENTS 1,932,228 A 10/1933 Postel
3,038,336 A 6/1962 Peters
(Continued)

FOREIGN PATENT DOCUMENTS

DE 3533070 A1 3/1987
EP 0996853 B1 10/2008
JP 54130958 10/1979

OTHER PUBLICATIONS

International Search Report and Written Opinion of PCT Application No. PCT/US2015/050450 dated Dec. 10, 2015: pp. 1-14, 2015.
(Continued)

*Primary Examiner* — John Fitzgerald
(74) *Attorney, Agent, or Firm* — K&L Gates LLP

(57) ABSTRACT

Disclosed are methods in which measurements are obtained from a plurality of sensors secured in spaced relation to one another across at least a portion of the depth of reservoir of some form in order to identify one or more characteristics of the fluids within the reservoir. The sensors are used to monitor ambient forces exerted by fluids within the tank proximate each sensor. An example mechanism for obtaining the measurements includes a plurality of sensors, such as strain gauges, supported on a structure that supports the sensors in fixed relation to one another, and can, in some examples, support the sensors in a known relation relative to boundaries of the reservoir.

20 Claims, 7 Drawing Sheets

(51) Int. Cl.
  *G01N 9/36* (2006.01)
  *G01N 33/28* (2006.01)

(56) References Cited

U.S. PATENT DOCUMENTS

| | | | |
|---|---|---|---|
| 3,153,342 | A | 10/1964 | Pierce |
| 3,169,396 | A | 2/1965 | Marius |
| 3,290,938 | A | 12/1966 | Miller |
| 3,583,221 | A | 6/1971 | Ehrenfried |
| 3,792,407 | A | 2/1974 | Ehrenfried |
| 4,043,193 | A | 8/1977 | Bailey |
| 4,142,415 | A | 3/1979 | Jung |
| 4,248,087 | A | 2/1981 | Dennis |
| 4,446,730 | A | 5/1984 | Smith |
| 4,553,216 | A | 11/1985 | Stevens |
| 4,625,548 | A | 12/1986 | Charter |
| 4,625,553 | A | 12/1986 | Charter |
| 4,711,117 | A | 12/1987 | Cosser |
| 4,770,050 | A | 9/1988 | Haefner |
| 4,984,468 | A | 1/1991 | Haefner |
| 5,026,984 | A | 6/1991 | Gerdt |
| 5,325,716 | A | 7/1994 | Haefner |
| 5,853,583 | A | 12/1998 | Shah |
| 5,944,418 | A | 8/1999 | Orr |
| 6,282,953 | B1 | 9/2001 | Benjey |
| 7,047,807 | B2 | 5/2006 | Woodard |
| 8,181,515 | B2 | 5/2012 | Stephens |
| 8,794,061 | B1 | 8/2014 | Sickels |
| 9,162,457 | B1 | 10/2015 | Li |
| 9,347,848 | B1 | 5/2016 | Westmoreland |
| 9,476,743 | B1 | 10/2016 | Westmoreland |
| 9,598,741 | B2 | 3/2017 | Ojeda Arroyo |
| 9,694,579 | B2 | 7/2017 | Li |
| 9,841,307 | B2 | 12/2017 | Hedtke |
| 11,555,733 | B2 * | 1/2023 | Beckett ............... G01F 23/363 |
| 2002/0124646 | A1 | 9/2002 | Mokuo |
| 2006/0010962 | A1 | 1/2006 | Rivas |
| 2007/0251317 | A1 | 11/2007 | Lopushansky et al. |
| 2008/0066555 | A1 | 3/2008 | Rezgui et al. |
| 2008/0156092 | A1 | 7/2008 | Boiarski |
| 2008/0223618 | A1 | 9/2008 | Warren |
| 2009/0272188 | A1 | 11/2009 | Byrne |
| 2009/0301190 | A1 | 12/2009 | Ross, Jr. |
| 2012/0298157 | A1 | 11/2012 | Noh |
| 2013/0042678 | A1 | 2/2013 | Studer |
| 2013/0118254 | A1 | 5/2013 | Urban |
| 2014/0208846 | A1 | 7/2014 | Gebhardt |
| 2015/0218667 | A1 | 8/2015 | Ojeda |
| 2016/0047683 | A1 | 2/2016 | Winkens |
| 2016/0167391 | A1 | 6/2016 | Li |
| 2016/0214381 | A1 | 7/2016 | Li |
| 2018/0313735 | A1 | 11/2018 | Gallagher |
| 2019/0056257 | A1 | 2/2019 | Bellmann |
| 2021/0148746 | A1 * | 5/2021 | Hallot .................. G01L 15/00 |

OTHER PUBLICATIONS

Fann Instrument Company, Slurry Sampler (Tulsa Oil Thief), Slurry Sampler (Tulsa Oil Thief), 2007, 2007: p. 1, 2007.

Izumo, Physical Quantity Measured by a Vibration Viscometer, Physical Quantity Measured by a Vibration Viscometer, Oct. 2006, 23rd Sensing Forum, Oct. 2006: pp. 1-9, 2006.

Lisco Analytical APS, Process Viscometers, Process Viscometers, Jan. 24, 2018, Jan. 24, 2018: pp. 1-5, http://www.liscotech.dk/en/products/process-viscometers., 2018.

* cited by examiner

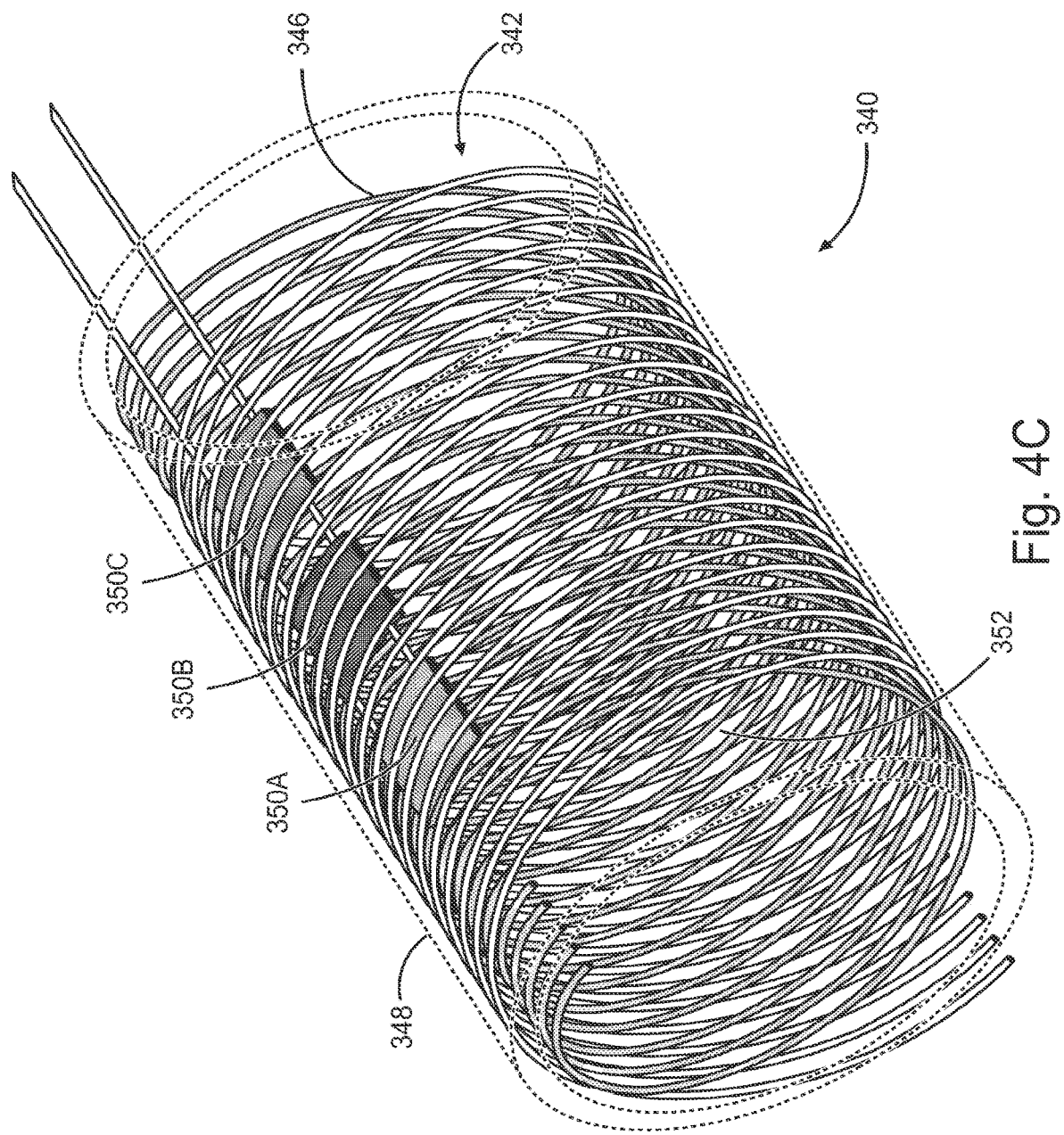

METHOD AND APPARATUS FOR MEASURING CHARACTERISTICS OF FLUID IN A RESERVOIR

BACKGROUND

This disclosure relates generally to methods and apparatus for measuring characteristics of fluids in a reservoir, for example as may be found in tanks, such as those known as "mud pits," as used in the oil and gas industry during the process of drilling of wells; and more specifically relates to methods and apparatus for measuring characteristics such as depth, volume, and others, such as, for example, fluid density.

Drilling fluid circulated down a drill string to lubricate the drill bit and remove cuttings is typically broadly referred to as drilling "mud." In the course of drilling a well, the drilling mud will be circulated downhole, returned to the surface, and then collected in one or more so-called "mud pits" or "mud tanks." In the course of such operations, densities of the fluids may change frequently due to various additives being introduced into the mud system, contaminants such as formation fragments remaining in the mud system, and/or additional fluids being introduced into the system. Although materials may be added to the mud system in the course of a drilling operation, the mud system is essentially a closed loop, in which changes in volume other than those resulting from materials intentionally introduced into the system, which are known quantities, can be indicative of a drilling anomaly, such as fluid incursion from the formation being drilled (typically referred to as a fluid "kick"), or a circulation loss, resulting from loss of a portion of the mud system into the formation being drilled.

Conventional techniques for measuring characteristics of fluids in a mud tank typically include taking physical samples and analyzing those relative to the characteristics of interest. Because these conventional techniques require manual action, they are relatively expensive to perform, and the analysis makes them impractical to perform as frequently as might be optimal. As a result, it would be beneficial to be able to measure characteristics of fluids within one or more mud pits at a well site such as depth, volume, and/or others such as weight, density, settling within the pit, circulation within the pit, etc., without the requirement of manual intervention.

BRIEF DESCRIPTION OF THE DRAWINGS

FIGS. 3A-C are schematic views of mud tank sensor assemblies similar to those of FIGS. 2A-B; in which FIG. 3A depicts a first embodiment depicted in horizontal cross-section; and FIG. 3B depicts a portion of the sensor of FIG. 3A in a partial side view indicating components therein; and FIG. 3C depicts an alternative example embodiment in horizontal cross-section.

FIGS. 4A-C are schematic representations of an alternative construction for tank sensor assemblies, in which FIG. 4A depicts a representative portion of the structure from a side view: FIG. 4B depicts a representative portion of the structure partially in vertical section: and FIG. 4C depicts the portion of the structure from an oblique perspective.

DETAILED DESCRIPTION

Figure 1:
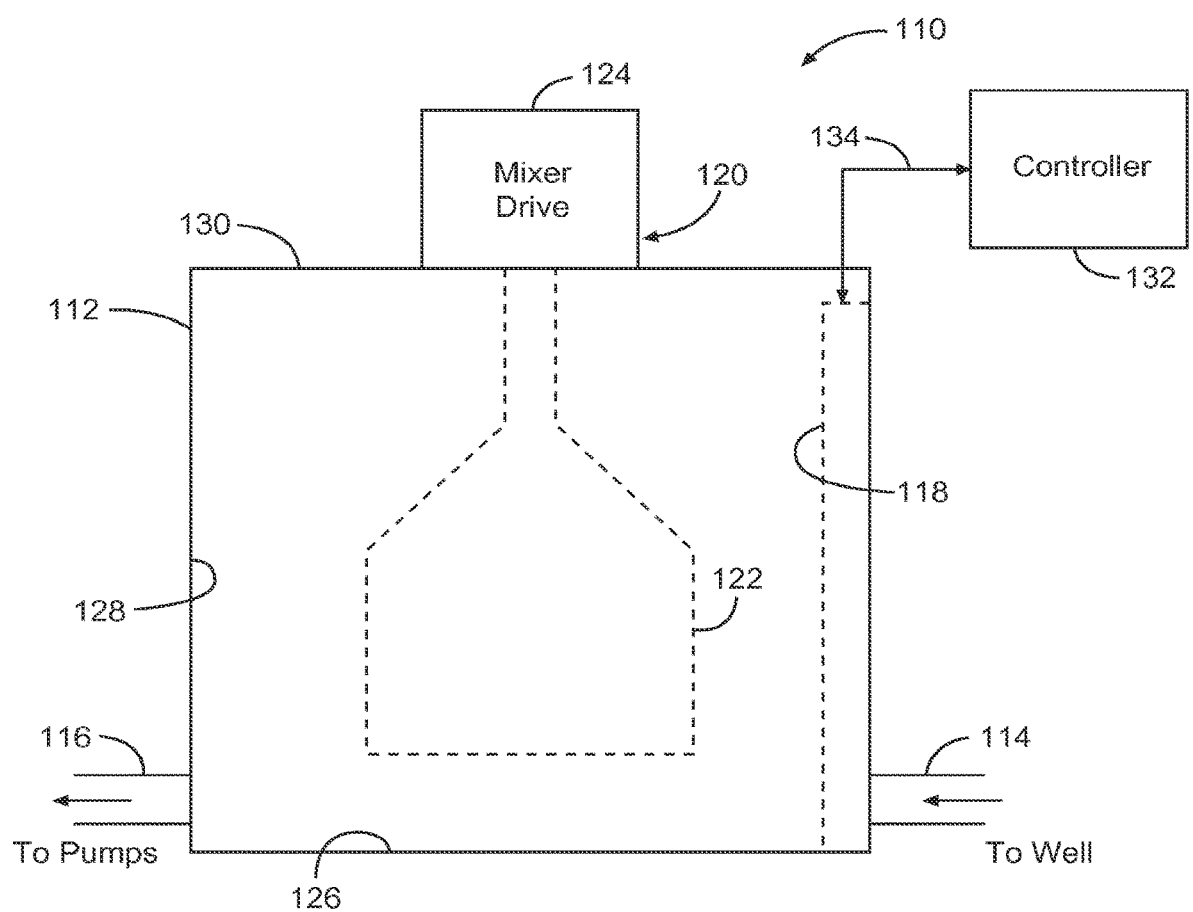
FIG. 1 is a schematic diagram of a mud tank including a sensor assembly therein, in one example configuration.

The present disclosure describes new methods and apparatus for measuring characteristics of fluids in a tank or other reservoir. The techniques and structures described and illustrated herein are believed to have particular benefit for use in reservoirs (such as "mud pits" or "mud tanks") used in the oil and gas industry in drilling operations, as described earlier herein. For efficiency of explanation such reservoirs, and all other reservoirs suitable for use with the described methods and apparatus, will be referred to herein generically as a "tank" or "tanks." The use of this terminology does not imply any specific structure or form to the reservoirs ("tanks"), or any distinction as to whether the reservoirs are naturally-occurring or man-made structures.

The new methods disclosed herein involve receiving measurements from a plurality of sensors secured in spaced relation to one another across at least a portion of the depth of the tank. The sensors may be of any of various forms such as are responsive to one or more parameters associated with the pressure of fluids within the tank, and are therefore suitable for providing an indication of the ambient forces exerted by fluids within the tank proximate each sensor. In many examples, a plurality of sensors of the same type and measurement capability will be used. The methods and apparatus described herein are believed to offer the capability for improved operations by eliminating the need to manually take fluid samples from the tank and perform analysis on those samples to determine the density and other properties of the fluids. Additionally, the described methods and apparatus make it much simpler to take periodic measurements to monitor the depth and/or volume of fluids in the tank, or characteristics of those fluids than is typically done when manual observation or sampling of the fluids is performed. As will be apparent to persons skilled in the art having the benefit of this disclosure, the described methods and apparatus may be used to take periodic measurements at any desired interval, for example every quarter hour, or every hour, in view of the simplified process for making measurements.

In some example systems, a plurality of strain gauges are supported within the reservoir in a manner by which they are responsive to pressure exerted by the fluid in the tank at the location of the sensor. In one example mechanism for providing this capability, the strain gauges will be supported on a sensor assembly which supports the sensors in fixed relation to one another. In some examples of such a support assembly, the strain gauges are each supported on the sensor assembly by being mounted to a deflection element having a surface that will deform in response to pressure from fluids in the tank acting on the deflection surface. In some examples, the deformable surface is an exterior surface of a structural element that will deflect under the fluid pressures present in the tank, and the strain gauges are operatively coupled to the opposing surface of the structural element, where the measured strain resulting from the deflection provides a measure of the fluid pressure causing the deflection. In some example configurations, the deformable surface is the exterior of a support assembly which provides an environment in which the sensors are located, and which may be filled with a desired fluid (including in some examples atmospheric air), against which the fluid pressures in the tank will act, through the deformable element. In some examples, all provided sensors will be mounted to a single deformable element: while in other examples, separate deformable elements may be provided for each sensor, or for a subset of the provided sensors. As will be addressed later herein, sensors other than strain sensors may be used to monitor deformation of the deformable element, such as capacitance sensors, Hall effect sensors, piezoelectric sensors, and other proximity sensors, etc.

In some example systems, depending upon the fluids within the tank, or expected to be within the tank, it may be desirable to provide mechanisms to assure full liquification of the fluids. For example, in a conventional mud tank environment some tanks will be expected to include drilling "mud" that will include not only a liquid component but also solids, and potentially other additives, including various polymers and other fluid conditioning materials. In some applications, these drilling muds may be maintained in a liquid state through circulation in the tank, either through use of pumping mechanisms or one or more mechanically driven impellers. However, other mechanisms may be desirable to assure liquification immediately proximate the sensors. In some embodiments this can be achieved by using a movable element, such as a vibratory element, proximate the sensors in combination with a drive mechanism to oscillate to achieve liquification of the surrounding fluid. In some examples, the movable element will be the deformable element associated with one or more sensors.

Referring now to the drawings in more detail, and particularly to FIG. 1, that figure depicts a schematic representation of an example mud tank 110 as may be used in well drilling operations. As will be apparent to persons skilled in the art, many configurations of tanks are known for such use; and in many examples, sequences of tanks may be provided, with each individual tank customized in overall configuration for a specific functionality. As a result, the methods and apparatus described herein should be understood to be suitable for use with a wide variety of tank configurations, including configurations having a substantially different structure than that illustrated. Tank 110 includes an enclosure, indicated generally at 112, that includes sidewalls 128 and a bottom surface 126 that define the container for holding fluid. Tank 110 includes an inlet 114 coupled to receive fluids from a well, and an outlet 116 which in many examples will be coupled to one or more pumps. Person skilled in the art will recognize that the inlet may not be coupled directly to a well, but may be coupled to other upstream tanks or other mechanisms located intermediate tank 110 and the well.

In this example, 110 also includes a mixer or circulation assembly, including an impeller, indicated in phantom at 122, and a drive assembly, indicated generally at 124, operably coupled to impeller 122 to move the impeller in a desired fashion. Tank 110 also includes a sensor assembly, indicated in phantom at 118, placed in one of many possible operating orientations, extending generally vertically along a portion of sidewall 128. In many examples, sensor assembly 118 will be placed in a position azimuthally offset from either tank inlet 114 or tank outlet 116. In the depicted example, sensor assembly 118 is schematically illustrated as extending from the bottom surface 126 of tank 110, to a position proximate the upper edge 130 of tank 110. However, sensor assembly 118 may be placed in many other orientations. For example, sensor assembly may extend generally diagonally relative to bottom surface 126 (or relative to another generally horizontal reference). Additionally, sensor assembly 118 does not have to extend from bottom surface 126, but may be supported at some selected distance above bottom surface 126. In most applications, it will be desirable to place sensor assembly 118 within a tank such that the sensors therein are at a known distance from bottom surface 126.

Sensor assembly 118 is coupled to a control unit 132 through a sensor bus 134. Control unit 132 may be a discrete unit essentially dedicated to controlling the sensors and/or making measurements in one or more mud tanks, or may be a controller also utilized to perform other wellbore drilling management functionality. Such control of the sensors will include the providing of any prerequisites to the sensors necessary for the sensors to receive and communicate measurements. Thus, such control implemented by the control unit, at its most basic level, will include providing any necessary power to the sensors, and may further include polling the sensors to cause them to acquire, retain, and/or transmit measurements to the control unit 132. Such control functionality may be implemented through use of several devices rather than just one, and thus the group of such devices providing the control functionality would correspond to the control unit identified in FIG. 1.

In the depicted example, only one sensor assembly 118 is depicted. However, multiple sensor assemblies may be included in a tank 110, with either all sensor assemblies being oriented in a similar manner in desired locations in the tank; or some sensor assemblies may be configured differently or oriented differently within the tank as compared to other sensor assemblies.

Figure 2A:
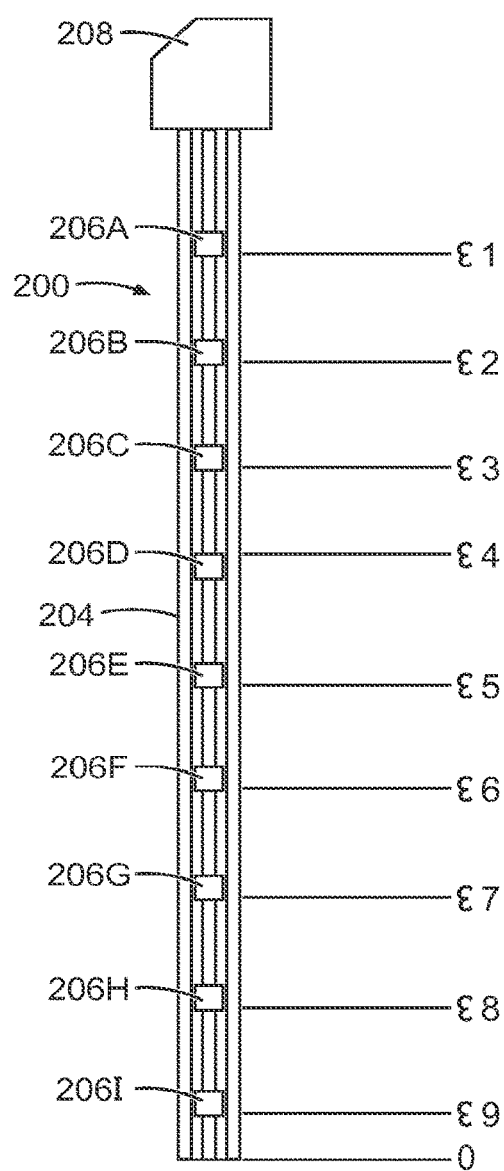
FIGS. 2A-B are schematic views of first and second alternative embodiments, respectively, of tank sensor assemblies.
Figure 2B:
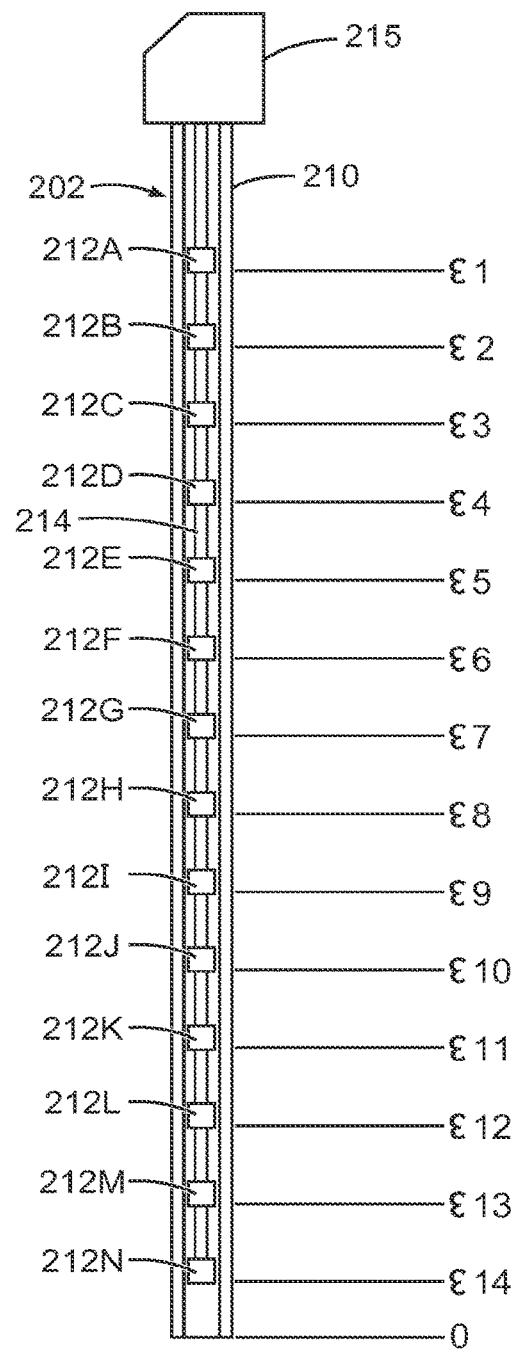

Referring now to FIGS. 2A-B, each figure depicts a respective example configuration for a sensor assembly, in which FIG. 2A depicts sensor assembly 200 which includes a plurality of sensors 206A-G arranged at a selected spacing interval; and in which FIG. 2B depicts sensor assembly 202 which includes a greater plurality of sensors 212A-N (i.e. 14 sensors) arranged at a relatively closer spacing interval relative to sensors 206A-G in sensor assembly 200. Each sensor assembly 200, 202 includes a respective support assembly, indicated generally at 204 and 210, respectively. Each sensor assembly 200, 202 also includes a respective communication controller, indicated generally at 208 and 215, respectively. As will be apparent from the discussion below, each support assembly 204, 210 can be of various possible configurations. Similarly, each communication controller 208, 215 can be of several possible configurations. For example, each communication controller can be very simple, providing primarily just electrical (or optical) connection between controller bus 134 and the sensors within each sensor assembly 200, 202; but in other examples can include one or more processors or controllers configured to control operation of the sensors and any other components the sensor assembly, examples of which are described below.

Both sensor assemblies 200, 202 are depicted as essentially linear structures, supporting the plurality of sensors on a common axis. This structure offers advantages both in simplification of correlating of the sensor measurements with one another, and relative to their relative depth within a tank, and also as to manufacturing, since a linear support structure can be utilized. However, other structures are possible and contemplated for use. For example, the sensor assemblies could support each sensor along essentially a stair step pattern, where each sequential sensor is horizontally offset from a sensor either above or below it.

In many examples, the sensors will be temperature-compensated, semiconductor strain gauges; which are available to address a range of potential strains as may be encountered within the tank environment with the specific configuration of sensor assembly utilized. However, as noted above, many alternative types of sensors may be used. Additionally, while it will very often be desirable to use identical sensors for sensing the fluids, there may be instances in which it is desirable to use two or more different types of sensors, such as for sensing other properties of the fluids.

Figure 3A:
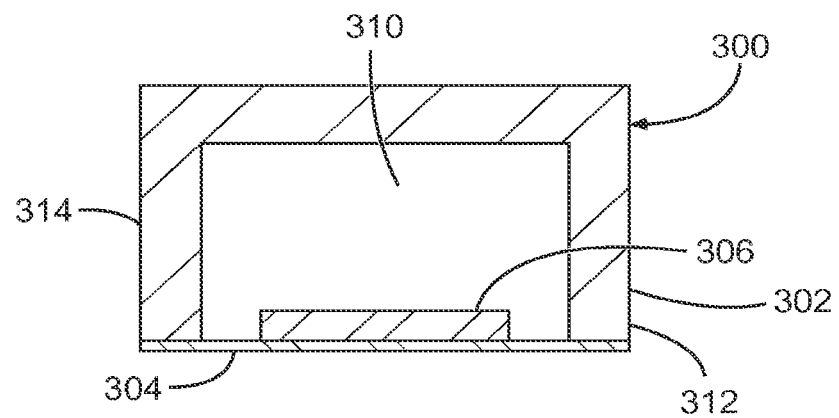
Figure 3B:
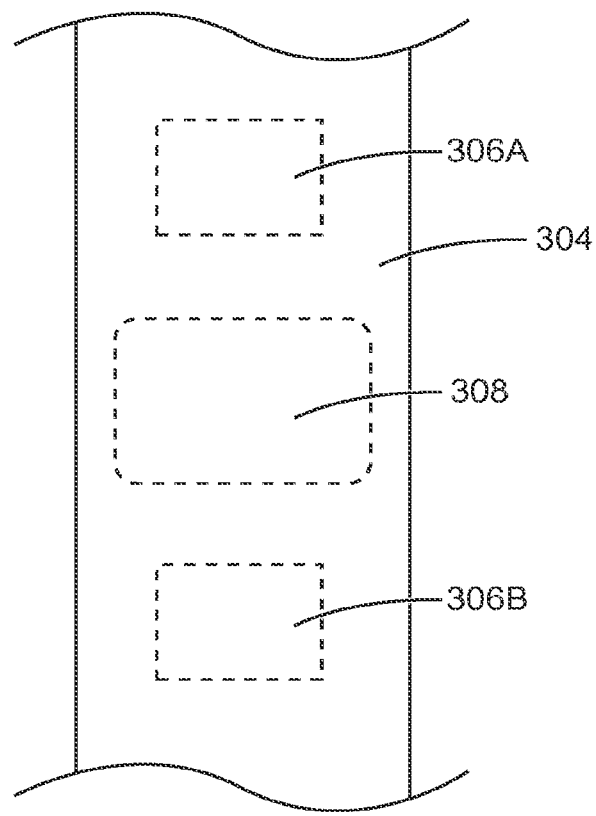
Figure 3C:
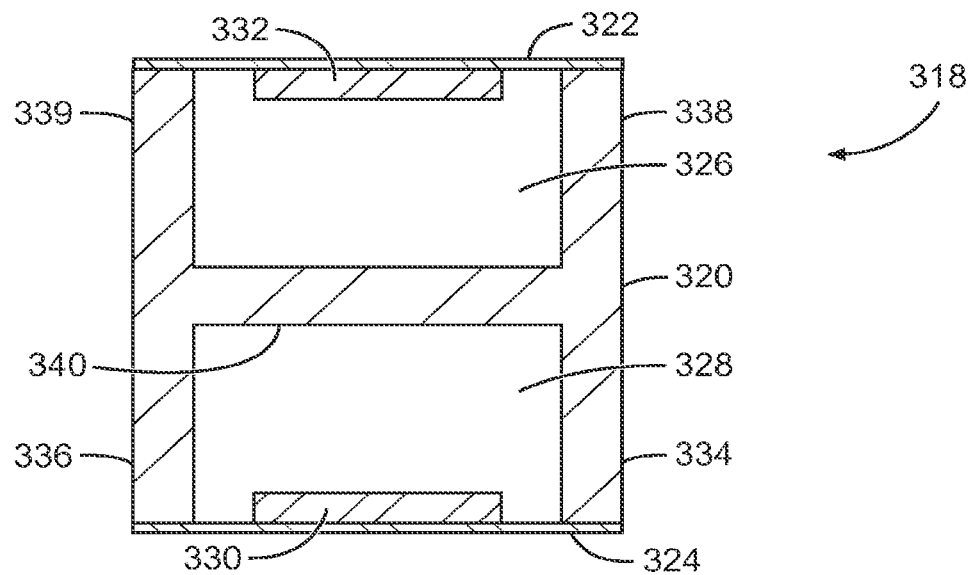

Referring now to FIGS. 3A-C, the figures depict schematic representations of alternative configurations of support assemblies suitable for use in a sensor assembly such as either of sensor assemblies 200, 202 in FIGS. 2A-B. FIGS. 3A-B depict a first embodiment of a support assembly 300, illustrated in FIG. 3A in a generally horizontal section, and illustrated in FIG. 3B in a partial side view. FIG. 3C depicts an example alternative configuration support assembly 318, illustrated in generally horizontal section.

Referring now specifically to FIGS. 3A-B, support assembly 300 includes a structural member 302 having a generally U-shaped cross-section. Structural member 302 may be formed of any suitable material which, in many example systems will be a generally rigid material, such as metal, or a composite material, for example such as fiberglass, carbon fiber, etc. For most systems, any generally rigid material suitable to withstand the fluids and pressures within the tank, may be used. Support assembly 300 also includes a deformable member 304 which engages each leg 312, 314 of the U-shaped cross-section to define a cavity 310 therein. In many example configurations, deformable member 304 will be sealingly coupled to legs 312, 314, such as through adhesives, mechanical fasteners, gasket material or any combination thereof, such that cavity 310 is isolated from fluids surrounding support assembly 300.

Deformable member 304, once again, can be of any material suitable for use in the chemical and pressure environment of fluids within the tank in which it will be placed, which has the further capability of deflecting in response to pressure in a predictable manner, such that a measurement of deflection can be correlated to a magnitude of fluid pressure causing the deflection. As noted earlier herein, the deflection may be sensed directly, such as through strain sensors secured to an interior surface of deformable member 304, as indicated at 306: it may also be detected by evaluating the proximity relative to a reference (thus, the deflection), such as through a capacitance sensor or a Hall effect sensor, as well as other possible sensing mechanisms. It is currently anticipated that a metal plate, formed of a selected material and thickness to deflect under the foreseeable pressures to which it will be subjected, will be a desirable structure for deformable member 304.

Referring now specifically to FIG. 3B, the figure depicts support assembly 300 in partial vertical section, looking at the surface of deformable member 304. A pair of spaced sensors 306A-B are depicted in phantom to indicate their relative positions behind deformable member 304. As noted earlier herein, in some operating environments, it may be desirable to assure liquification of fluids immediately adjacent sensors 306A-B. One example mechanism for achieving this is through oscillation of deformable member 304 through an appropriate drive structure, as indicated generally at 308. Drive structure 308 maybe for example a voice coil supported within cavity 310 and arranged to cause oscillation of deformable member 304, to assure full liquification of fluids adjacent deformable member 304. Accordingly, as will be apparent to persons skilled in the art having the benefit of this disclosure, the nature of the fluids in the tank may dictate different frequencies of oscillation to assure optimal liquification.

For some systems, it may be desirable to have sensors which provide a relatively large area of sensing, for example across about a 2 inch or larger dimension. In some example systems having a form generally as discussed in reference to FIGS. 3A-B, the sensors may be configured to measure essentially across the deflectable width of the deformable member to which they are attached. The specific configuration and dimension of the sensors utilized may also impact the selection of the dimension, characteristics and spacing of the drive structure for oscillating the deformable member. Additionally, a different number or spacing of drive structures may be dictated where multiple deformable members, each supporting one or more sensors, are utilized rather than a single deformable member supporting all sensors.

Referring now specifically to FIG. 3C, the Figure depicts an alternative configuration for support assembly 318, again in essentially horizontal section. Support assembly 318 includes a support element 320 having a generally H-shaped cross-section essentially, as is commonly associated with a so-called I-beam. This example configuration is analogous to having two support assemblies 300 of the preceding figures arranged in opposing orientation to one another. In this arrangement, two deformable members 322, 324 are coupled across pairs of legs 334 and 336, and 338 and 339, extending from central web 342, respectively, to define cavities 326, 328 therein. With this configuration, in many examples, sensors 330, 332 will be placed to sense deflection of both deformable members 322, 324, as shown by placement of sensor 330 on deformable member 324, and by placement of sensors 332 on deformable member 322. With the configuration of support assembly 318, sensors on opposing sides of the assembly will, in some examples, be placed at a common vertical dimension along support assembly 318; but in other examples, may be staggered between sides, with sensors on one side vertically offset from sensors on the other side.

This configuration can offer many potential advantages. For example, in tanks in which the fluid is circulating, either through actions of pumps or through movement of an impeller, as discussed relative to FIG. 1 herein, this movement can create localized pressures in excess of those that would be experienced if the fluid was static. Thus, while the pressure exerted by the fluid can be correlated to the weight of the fluid, and with identification of the approximate volume within the tank can be correlated with the fluid density: where fluid movement results in pressures in excess of those of the static weight of the fluid such correlations could be less than ideally accurate. However, by using sensors in opposed orientation relative to surrounding fluids, the identified pressures determined in response to the deflection measured by the sensors may be correlated with one another to adjust for such dynamic forces. In other examples, such as those as described above where the sensors on a first side of the support assembly are staggered relative to sensors on the other side, the sensors may be used to provide greater granularity in measurement of deflection. Additionally, some combination of these measurements may be used.

Figure 4A:
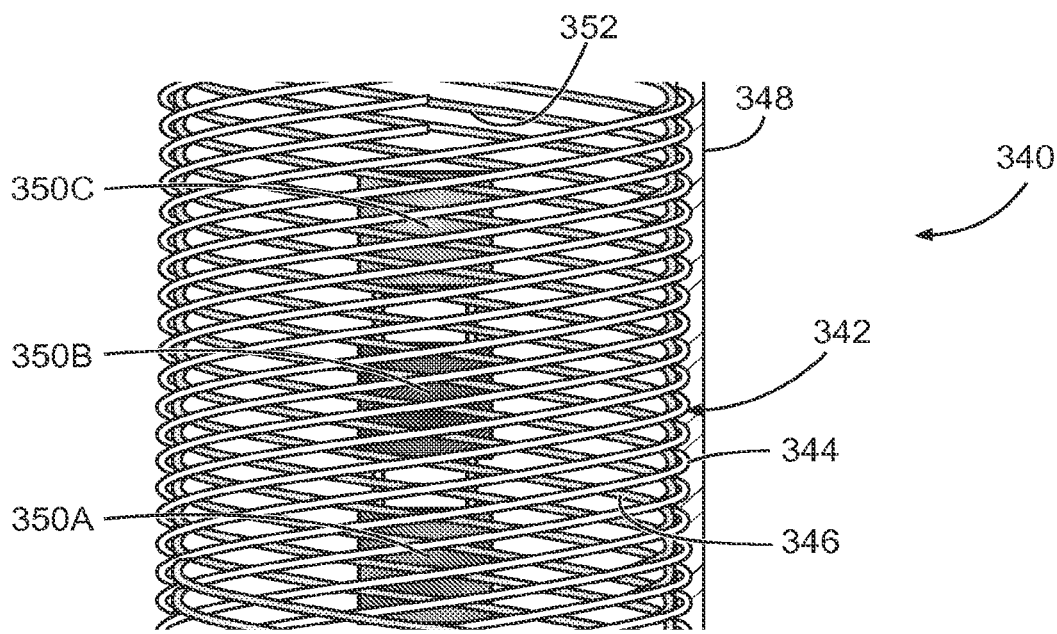
Figure 4B:
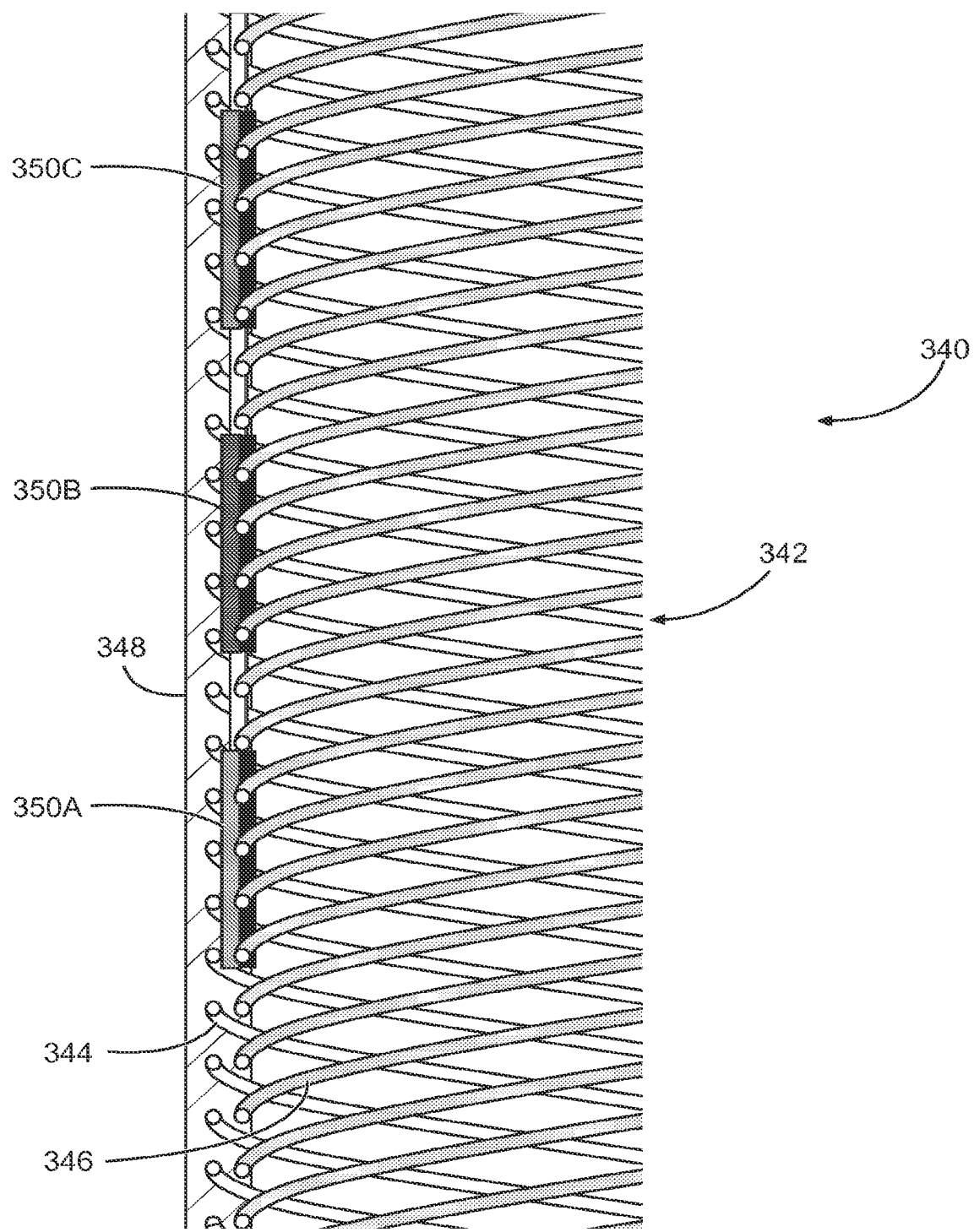

Referring now to FIGS. 4A-C, these figures depict an alternative structure for a support assembly, indicated generally at 340. Support assembly 340 includes a support member 342 including one or more coils of composite material, such as, for example, coils of carbon fiber. Support assembly 340 includes two such coils 344, 346, which in this example are oriented with the rise of the respective coils oriented in opposing directions, to form a basket-like pattern, and which are secured in position by a generally flexible resin or other encapsulant material suitable for use in the tank environment as a deformable member, as indicated at 348. Such encapsulant material can be, for example, epoxy, polyester, acrylic, urethane, rubber, silicone and derivatives or combinations thereof. This structure provides a solid cylinder that may be closed relative to the environment to define an interior cavity 352 (as best seen in FIG. 4C), analogous to those described relative to FIGS. 3A-C.

A plurality of sensors 350A-C are supported in support assembly 340, and are at least partially encased within the resin, along with appropriate conductors (for example, either electrical or optical) to communicate signals from the sensors to a communication mechanism, such as a communication controller associated with the sensor assembly (as described relative to FIGS. 2A-B, at elements 208, 215).

Figure 5:
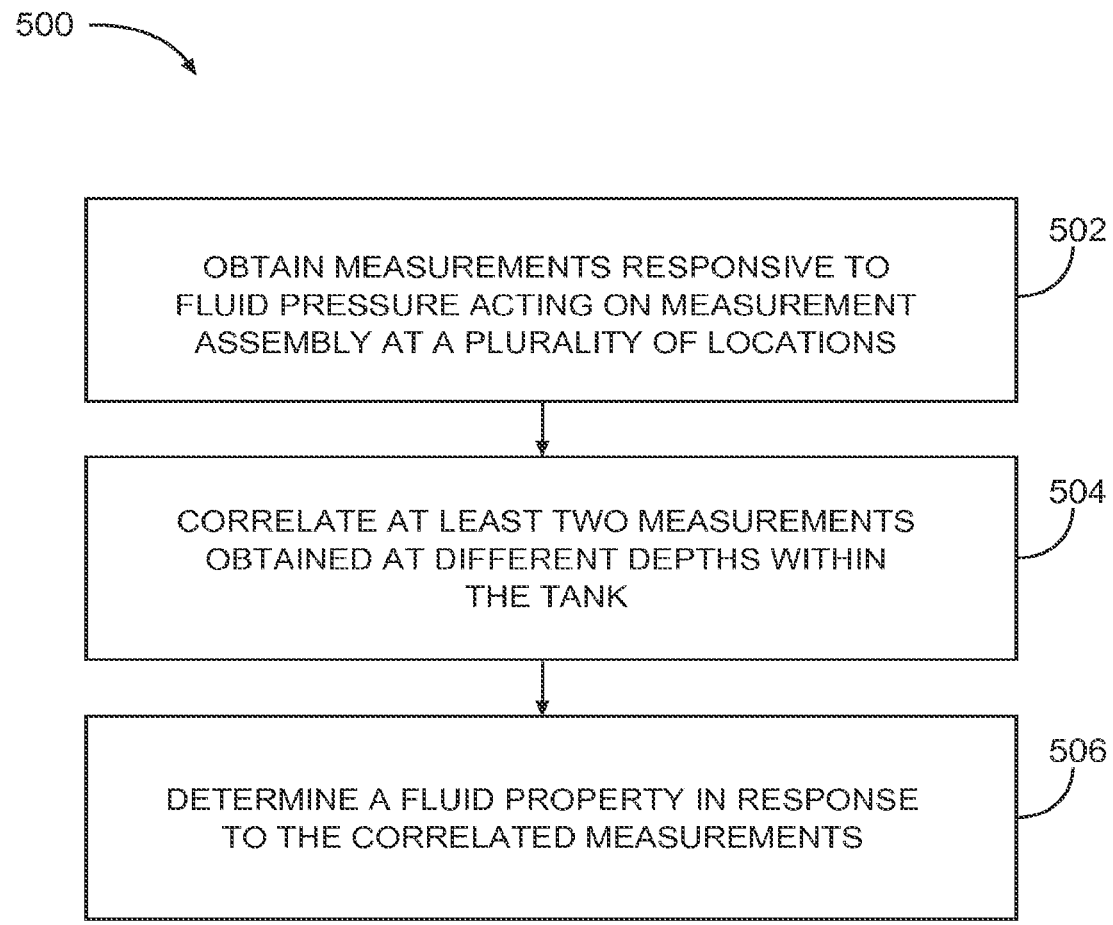
FIG. 5 depicts a flow chart of an example method for evaluating fluids within the tank.

Referring now to FIG. 5, the figure depicts a flowchart of one example method 500 of evaluating fluids within a tank. In the depicted method, in a first step, indicated generally at 502, measurements are obtained a fluid pressures acting on a measurement assembly, at a plurality of locations along the assembly. In some configurations, the measurements will the obtained from sensors supported on a measurement assembly, such as, or analogous to, those depicted in FIGS. 2A-B (at 200 and 202), and described in relation thereto. In other configurations, the sensors might not be located on a discrete measurement assembly but could be installed in selected locations across some portion of the depth of a tank, and operatively coupled to appropriate components to receive signals from the sensors, and where desired, to provide control signals thereto (as well as to other components that may be associated with the sensor assemblies, for example vibration mechanisms, as described earlier herein).

In the next step of the method, indicated at 504, at least two measurements obtained at different depths within the tank will be correlated to one another. From the correlation, at least one fluid property of the fluid in the tank will be determined, as indicated at 506. As referenced earlier herein, measurements of observed deflections of one or more members at different depths in the tank can each be correlated to an indication of the observed pressure at each depth. These observed pressures at two or more depths can then be correlated to identify different fluid properties. For example, the top of the fluid, indicative of the total volume of fluid within the tank can be identified. Measurements from strain gauges ($\varepsilon_i$) starting from the bottom across at least some portion of the depth of a tank are indicative of the top of fluid in the tank, as indicated by the relation:

$$(\varepsilon_i - \varepsilon_{i+1}) > (\varepsilon_{i+1} - \varepsilon_{i+2}) \qquad \text{eq. 1}$$

In which, $\varepsilon_{i+1}$ will represent the location of the gauge just below the top of fluid when the Eq.1 hold true (as the expression is evaluated starting from the bottom gauge of the tank), then the gauge i+1=n, where n is the number of gauges below the fluid-air interface.

In some cases, it may be useful to express Eq.1 with a correction factor to account for settling in the fluid.

$$(\varepsilon_i - \varepsilon_{i+1}) > (\varepsilon_{i+1} - \varepsilon_{i+2}) * C \qquad \text{eq. 2}$$

C can be in based on the statistical analysis strain differentials or default to 1. Thus, the tank depth can be determined, such as through the relation:

$$\text{Tank depth} = D = [(n * \ell_0 + \ell')] * \sin\theta \qquad \text{eq. 3}$$

Wherein:

n represents the number of gauges below the fluid/air interface (i.e., the top of fluid), and thus $\varepsilon_n$ represents strain measurement just below the fluid/air interface; and the functional length of the sensor assembly may be represented by:

$$\text{functional length } \ell' = \frac{(\varepsilon_n - \varepsilon_{n+1})}{(\varepsilon_{n-1} - \varepsilon_n)} * \ell_0 \qquad \text{eq. 4}$$

wherein, $\ell_0$ represents the distance between each pair of gauges of the sensor assembly (in ft.). In this simplified case, the distance between the lowermost gauge and tank bottom was also considered to be $\ell_0$. If the distance between the lowermost gauge and tank bottom differs from $\ell_0$, then eq. 2 will need to be adjusted to account that variation. In other examples, the top of fluid may be determined by comparing one or more sensor measurements to a reference value to identify the sensor or sensors exposed to atmospheric conditions as opposed to fluid conditions; though this method may offer less accuracy than the methodology described above.

The fluid density ("MW") in the tank can also be determined from measurements made through a group of sensors arrayed across at least a portion of the depth of a tank (preferably including at least 2 sensors, and ideally more). These sensor measurements are correlated with the distance between the sensors, and the location of the sensors within the tank, such as though the following relation (this example assumes a linear array of sensors, such as through use of a sensor assembly as discussed earlier herein, though such a linear array is not required, as noted above):

$$\text{MW} = \frac{(\varepsilon_i - \varepsilon_{i-1}) * k}{0.052 * (\ell_0 * \sin\theta)} \qquad \text{eq. 4}$$

wherein:

MW is indicated in lbm/gal;

k represents a calibration constant to convert $\varepsilon_i$ to pressure equivalent units of psi; and θ represents the inclination of the sensor assembly in degrees.

In addition to the above fluid characteristics, other fluid characteristics may be determined based upon the above measurements, such as fluid viscosity. Additionally, a difference between observed pressures between vertically adjacent sensors within the fluid level can be used indicate "sag," or the settling level of solids within the mud tank. For example, a change in the slope of plotted received measurements would indicate a change in apparent fluid properties, particularly density, which could represent either settling of solids or separation of fluid components within the mud tank. Additionally, in a system as described above in which the sensor support assembly includes the capability of oscillating a surface to promote liquification to eliminate gel structures that may affect the density measurements.

In the above example of using the described structures to make a measurement of viscosity, the described mechanisms described for use in liquification of the fluids surrounding one or more sensors may be controlled to induce a specific vibration of a deformable member as described earlier herein (such as deformable member 304 in FIG. 3), to serve as a vibrational viscometer. Such an oscillating surface can be used in various ways to serve as a vibrational viscometer for the fluids adjacent the surface. As one example, the amplitude of vibration in response to a given input will be dependent upon the viscosity of the surrounding fluid providing a resistance to such vibration. A sensor assembly (such as discussed at 200 or 202 in FIGS. 2A-B) can be configured to monitor the amplitude of oscillation of the deformable member of one or more sensors (such as indicated at 206 in FIG. 2A; and at 121 in FIG. 2B), and also to measure the power output required to keep the oscillation drive mechanism vibrating at a given amplitude. The power level can be compared to reference levels, such as empirically determined values, which can be contained in a lookup table, to provide a measure of viscosity. Another alternative methodology is to measure the decay of the oscillation as the excitation is switched off as a function of time. Generally, fluids with a relatively lower viscosity will allow the signal to decay more slowly than will fluids of a relatively higher viscosity. Again, a measured vibratory response after the end of the oscillation input can be compared to a reference value, such as in a lookup table, to provide a measure of viscosity. As one additional example, vibrational response may be monitored through use of two or more sensors. In one example of such a system, the deformable member of one sensor may be driven with the oscillatory drive signal, and the vibration induced at another sensor monitored, such as at a neighboring sensor above or below the driven sensor, such that the induced vibration frequency can be measured as a function of phase angle relative to the oscillatory drive signal. Again, this measurement may be compared to previously determined values to provide a measure of viscosity.

In many applications, it will be advantageous to make such viscosity measurements at a plurality of depths within the tank. Such measurements will provide an indication of any stratification in the tank and of the viscosities of the stratified layers. Additionally, structures described herein facilitate making these viscosity measurements at any desired time or at any desired time interval(s); thereby further improving monitoring of the fluids in the mud tank, and of their properties and condition. In the case of viscosity measurements, the operation of one or more sensors to form a vibration viscometer does not necessarily require the correlation of sensor measurements from different depths within a tank, as described relative to the method of FIG. 5.

The ability to identify the fluid characteristic of the top of fluid facilitates "kick detection," as referenced earlier herein. Because a well mud system is essentially a closed system, subject to known volumes of material being added at the surface, a change in the top of fluid in the mud tank can be used to indicate fluid incursion from the formation (fluid "kick"), or "lost circulation" resulting from fluid loss into the formation. From development to this point, it appears possible to achieve resolution of the top of fluid within about 1 inch, based on an anticipated sensor spacing of approximately 12 inches in a mud tank having a height of approximately 8 ft, this would represent a resolution on the order of approximately 10 barrels out of a 500 barrel mud tank.

In many examples, the correlation of the measurements from the individual sensors within the tank will be performed by a controller, operatively coupled to the sensors (such as indicated at 132 in FIG. 1). Such a controller can be of many possible configurations, including a hardwired or otherwise single-purpose device, but in many examples will be a "processor-based system" including one or more microprocessors, microcontrollers and/or digital signal processors or other devices having the capability of running a set of executable machine code instructions (i.e., a "program"), which includes user-level applications as well as system-directed applications or daemons. Such a processor-based system will access a program stored on a machine-readable storage mechanism, which may be any form of storage media (either as a single medium or multiple media), in all forms: e.g., a centralized or distributed database and/or associated caches and servers; one or more storage devices, such as storage drives (including e.g., magnetic and optical drives and storage mechanisms), and one or more instances of memory devices or modules (whether main memory, cache storage either internal or external to a processor, or buffers); and thus includes any tangible medium which is capable of storing or encoding a sequence of instructions for execution by the machine (i.e. all are "non-transitory" devices), and that cause the machine to perform any one of the described methodologies. The term "non-transitory medium" expressly includes all forms of storage drives (optical, magnetic, etc.) and all forms of memory devices (e.g., DRAM, Flash (of all storage designs), SRAM, MRAM, phase change memory, etc., as well as all other structures designed to store information of any type for later retrieval.

For the avoidance of any doubt, the described methodology may be performed through a plurality of sensors supported within a tank, without regard for whether they are individually secured within the tank, or mounted to some form of support structure, such as the examples described herein. Additionally, where utilized, such a support structure can be of any suitable configuration, and, for example, may include features of any one or more of the various example support structures described herein. Additionally, any of the described measurements may be made in combination with one another, or individually; and may be made essentially simultaneously, or on different schedules, and may be desired for any particular situation.

Many variations may be made in the structures and techniques described and illustrated herein without departing from the scope of the inventive subject matter. Accordingly, the scope of the inventive subject matter is to be determined by the scope of the following claims and all additional claims supported by the present disclosure, and all equivalents of such claims.

What is claimed is:

1. A sensor assembly for identifying at least one characteristic of a fluid in a tank other than fluid level, comprising:
   a support assembly extendable into the tank and comprising a structural member and a deformable member that deforms in response to pressure, the deformable member being engaged with the structural member to define a cavity extending along the support assembly;
   sensors spaced within the cavity and supported by the deformable member, the sensors being operable to measure deformation of the deformable member in response to the fluid within the tank acting on the deformable member;
   a drive structure coupled to the support assembly and operable to oscillate the deformable member to liquefy the fluid adjacent the deformable member; and
   a control unit coupled to and operable to receive signals from the sensors and to correlate the signals to identify at least one characteristic of the fluid in the tank other than fluid level.

2. The assembly of claim 1, wherein the structural member is formed of a rigid material.

3. The assembly of claim 1, wherein the deformable member is deflectable in response to pressure in a predictable manner, such that a measurement of the deflection can be correlated to a magnitude of fluid pressure causing the deflection.

4. The assembly of claim 1, wherein the sensors operable to measure the deformation of the deformable member directly.

5. The assembly of claim 1, wherein the sensors are operable to measure the deformation of the deformable member by evaluating the proximity relative to a reference.

6. The assembly of claim 1, wherein the drive structure is operable to oscillate the deformable member at different frequencies depending on the nature of the fluid in the tank may.

7. The assembly of claim 1, wherein the drive structure is supported by the deformable member and located between two sensors.

8. The apparatus of claim 1, wherein the sensors may be sized and operable to measure across the deflectable width of the deformable member.

9. The assembly of claim 1, further comprising more than one support assembly, each support assembly including sensors.

10. The assembly of claim 1, wherein the control unit is operable to correlate the measurements from the sensors to identify the fluid level in the tank.

11. The assembly of claim 1, wherein the structural member comprises a U-shaped cross-section with legs and the deformable member engages each leg to define the cavity therein.

12. The assembly of claim 11, wherein the deformable member is sealingly coupled to the legs such that cavity is isolated from the fluid surrounding support assembly.

13. A sensor assembly for identifying at least one characteristic of a fluid in a tank other than fluid level, comprising:
 a support assembly extendable into the tank and comprising a structural member and deformable members that deform in response to pressure, the deformable members being engaged with the structural member to define a cavities extending along the support assembly;
 sensors spaced within each cavity and supported by the deformable members, the sensors being operable to measure deformation of the deformable members in response to the fluid within the tank acting on the deformable members;
 a drive structure coupled to the support assembly and operable to oscillate one of the deformable members to liquefy the fluid adjacent the deformable member; and
 a control unit coupled to and operable to receive signals from the sensors and to correlate the signals to identify at least one characteristic of the fluid in the tank other than fluid level.

14. The assembly of claim 13, wherein the structural member comprises two pairs of legs extending from a central web and the deformable members are each coupled across one of the pair legs to define the cavities therein.

15. The assembly of claim 13, wherein the sensors supported by each deformable member are placed at a common vertical dimension along support assembly.

16. The assembly of claim 13, wherein the sensors are supported on the deformable members in opposed orientation relative to the surrounding fluid and operable to identify pressures of the fluid in response to the deflection of the deformable members that may be correlated with one another to adjust for pressures in excess of those of the static weight of the fluid due to movement of the fluid in the tank.

17. The assembly of claim 13, wherein the control unit is operable to correlate the measurements from the sensors to identify the fluid level in the tank.

18. A method of identifying a characteristic of a fluid within a tank other than fluid level, comprising:
 controlling sensors secured in spaced relation to one another at respective depths within the tank and coupled to support assembly comprising a structural member and a deformable member engaged with the structural member to define a cavity;
 oscillating the deformable member to liquefy the fluid adjacent the deformable member;
 receiving measurements from the sensors in response to the deformation of the deformable member in response to pressure of the fluid within the tank; and
 correlating the received measurements to identify a characteristic of the fluid within the tank other than fluid level.

19. The method of claim 18, further comprising correlating the received measurements to identify the fluid level within the tank.

20. The method of claim 18, wherein the sensors are supported on multiple deformable members in opposed orientation relative to the surrounding fluid and wherein correlating further comprises adjusting for pressures in excess of those of the static weight of the fluid due to movement of the fluid in the tank.

* * * * *

UNITED STATES PATENT AND TRADEMARK OFFICE
CERTIFICATE OF CORRECTION

PATENT NO. : 11,739,636 B2  
APPLICATION NO. : 17/182978  
DATED : August 29, 2023  
INVENTOR(S) : Dale E. Jamison et al.

It is certified that error appears in the above-identified patent and that said Letters Patent is hereby corrected as shown below:

In the Claims

In Claim 6, Column 11, Line 6: "frequencies depending on the nature of the fluid in the tank may." should read "frequencies depending on the nature of the fluid in the tank."

Signed and Sealed this  
Twenty-sixth Day of September, 2023

Katherine Kelly Vidal  
*Director of the United States Patent and Trademark Office*